United States Patent

Strehlke et al.

[11] 4,006,243
[45] Feb. 1, 1977

[54] AMINO-, MERCAPTO- AND -OXY-SUBSTITUTED-PHENYL AND -PHENALKYL IMIDAZOLES

[75] Inventors: Peter Strehlke; Hans-Joachim Kessler; Ulrich Redmann, all of Berlin, Germany

[73] Assignee: Schering Aktiengesellschaft, Berlin & Bergkamen, Germany

[22] Filed: Apr. 11, 1975

[21] Appl. No.: 567,361

[30] Foreign Application Priority Data

Apr. 11, 1974 Germany .......................... 2418502
Mar. 7, 1975 Germany .......................... 2510781
Mar. 6, 1975 Germany .......................... 2510130

[52] U.S. Cl. ..................... 424/273; 260/295.5 S; 260/309
[51] Int. Cl.² ............. C07D 233/60; C07D 233/56
[58] Field of Search ................... 260/309; 424/273

[56] References Cited

UNITED STATES PATENTS

| | | |
|---|---|---|
| 3,711,487 | 1/1973 | Draber et al. ...................... 260/309 |
| 3,769,422 | 10/1973 | Timmler et al. .................... 424/273 |
| 3,833,603 | 9/1974 | Buchel et al. ...................... 260/309 |
| 3,927,017 | 12/1975 | Heeres et al. ...................... 260/309 |

FOREIGN PATENTS OR APPLICATIONS 2,130,673  12/1971  Germany .......................... 260/309

OTHER PUBLICATIONS

Cannon et al., Chem. Abst. 1958, vol. 52, Cols. 8124–8125.

*Primary Examiner*—Natalie Trousof
*Attorney, Agent, or Firm*—Millen & White

[57] ABSTRACT

Compounds of the formula

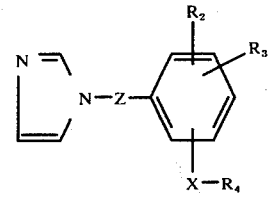

wherein Z is a direct bond or alkylene of 1 – 3 carbon atoms which is unsubstituted or substituted on the carbon atom alpha to the phenyl group by alkyl or unsubstituted or substituted phenyl, $R_2$ and $R_3$ singly are H, alkyl, alkoxy, alkylmercapto, halo, nitro or, collectively, $C_4H_4$, and $R_4$ is alkenyl, alkinyl, unsubstituted or substituted phenyl or phenylalkyl, or, when Z is substituted methylene, also alkyl, are useful in combating Germatophyte infections, especially *Trichophyton rubrum* and mentagrophytes, and yeast infections, especially *Candida albicans*, as well as bacterial and fungal infections.

136 Claims, No Drawings

AMINO-, MERCAPTO- AND -OXY-SUBSTITUTED-PHENYL AND -PHENALKYL IMIDAZOLES

BACKGROUND OF THE INVENTION

This invention relates to novel imidazoles.

Hydroxybenzylimidazole derivatives are known from the literature [Bull. Soc. Chim. France 1973, 1179] without any disclosure regarding their pharmacological activity.

A Russian work [Khim. Geterotsikl. Soedin. 2 : 209–213 (1970); C.A. 65, 13686] describes (1-imidazolyl)-anisoles, and Dutch Patent 67 16722 claims, in addition to these last-mentioned compounds, alkyl ethers generally. Methyl ethers of 1-phenethylimidazole are known. J. Org. Chem. 22, 1323–26 (1957). These are disclosed as useful, for example, as bronchodilatory agents, local anesthetics and diuretics.

SUMMARY OF THE INVENTION

In a composition aspect, this invention relates to compounds of the general Formula I

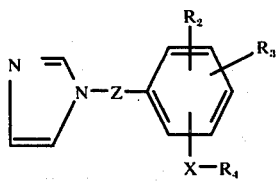

wherein Z is a direct bond or

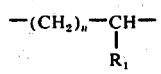

wherein $n$ is the integer 0, 1 or 2 and $R_1$ is a hydrogen atom, alkyl of 1–6 carbon atoms, phenyl, phenyl substituted by halogen, alkyl of 1–6 carbon atoms, alkoxy of 1–6 carbon atoms, or nitro; $R_2$ and $R_3$, which can be alike or different, are hydrogen atoms, alkyl of 1–10 carbon atoms, alkoxy of 1–6 carbon atoms, alkylmercapto of 1–6 carbon atoms, halogen atoms, or nitro, or collective are $C_4H_4$; $R_4$ is alkenyl of 3–6 carbon atoms, alkinyl of 3–6 carbon atoms, phenyl, phenyl substituted by at least one of halogen, nitro, trifluoromethyl, alkyl of 1–6 carbon atoms and alkoxy of 1–6 carbon atoms, or phenylalkyl of 1–4 carbon atoms in the alkyl group and the phenyl group is unsubstituted or substituted by at least one of halogen, nitro, trifluoromethyl, alkyl of 1–6 carbon atoms and alkoxy of 1–6 carbon atoms and, when $n$ is 0, $R_4$ additionally can be alkyl of 1–6 carbon atoms; and X is O, S or NH; and the physiologically acceptable acid addition salts thereof.

In another composition aspect, this invention relates to pharmaceutical compositions comprising a compound of Formula I.

In a process aspect, this invention relates to the use of compounds of Formula I to combat infections.

In another process aspect, this invention relates to a process for the production of compounds of Formula I comprising a. reacting a compound of general Formula II

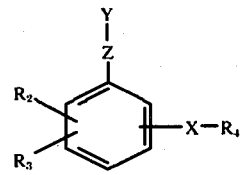

wherein Z, $R_2$, $R_3$, $R_4$ and X have the values given above and Y is a halogen atom, a reactive ester group or, when $n$ in Z equals 0, also hydroxy, with imidazole or an alkali salt of imidazole; or b. a compound of general Formula III

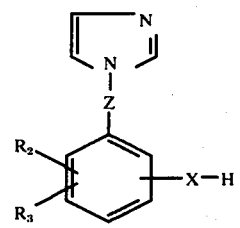

wherein Z, $R_2$, $R_3$ and X have the values given above, or an alkali salt thereof, is reacted with a compound of general Formula IV $$Q - R_4 \quad IV$$

wherein $R_4$ has the values given above and Q is a halogen atom or a reactive ester group; and thereafter a compound obtained according to (a) and (b) are optionally converted into a physiologically compatible salt thereof.

DETAILED DISCUSSION

Examples of classes of compounds of this invention embraced by Formula I are those wherein:

a. Z is a direct bond;
b. $n$ is 0;
c. $n$ is 1;
d. $n$ is 2;
e. in each of (b), (c) and (d), $R_1$ is H;
f. in each of (b), (c) and (d), $R_1$ is alkyl;
g. in each of (b), (c) and (d), $R_1$ is phenyl or substituted phenyl;
h. in each of (a) – (g), $R_4$ is alkenyl;
i. in each of (a) – (g), $R_4$ is alkynyl;
j. in each of (a) – (g), $R_4$ is phenyl or substituted phenyl;
k. in each of (a) – (g), $R_4$ is phenylalkyl with unsubstituted or substituted phenyl;
l. $n$ is O and $R_4$ is alkyl and $R_1$ is H, alkyl, phenyl or substituted phenyl;
m. X is O in each of (a) – (l);
n. X is S in each of (a) – (l); and
o. X is NH in each of (a) – (l).

When $R_1$ or $R_4$ is alkyl, the alkyl group can be straight chain or brached, lower or intermediate alkyl. Those of 1 – 6 carbon atoms are preferred, e.g., methyl, ethyl, propyl, isopropyl, n-butyl, tert.-butyl and n-hexyl.

When $R_2$ or $R_3$ is alkyl, the alkyl groups can be straight-chain or branched, lower or intermediate alkyl of 1 – 10 carbon atoms, such as, for example, methyl, propyl, isopentyl, n-hexyl, n-octyl, 1,1,3,3-tetramethylbutyl, and n-decyl. Preferred are those of 1 – 8 carbon atoms.

The alkyl group of the alkoxy and alkylmercapto groups are the above-defined alkyl groups of 1 – 6 carbon atoms.

The halogen atoms can be fluorine and iodine but preferably are bromine and chlorine.

Alkenyl groups of 3–6 carbon atoms can be straight-chain and branched and preferably are of 3–4 carbon atoms, such as, for example, allyl, 2-butenyl, 3-butenyl, 1-methylpropenyl and 2-methylpropenyl.

Examples of alkinyl groups of 3–6 carbon atoms are straight-chain and branched alkinyl of preferably 3–4 carbon atoms, such as, 2-propinyl, 2-butinyl, 3-butinyl, and 1-methyl-2-propinyl.

The alkyl portion of the phenylalkyl $R_4$ groups can be straight-chain or branched of 1–4 carbon atoms. Examples of such phenylalkyl groups are 1-phenylethyl, 1-phenyl-2-propyl, 2-phenyl-1-propyl, 2-phenyl-2-propyl, 1-phenyl-1-butyl, 1-phenyl-2-butyl, 2-phenyl-2-butyl, 3-phenyl-2-butyl, 4-phenyl-2-butyl, 2-methyl-1-phenyl-1-propyl, and 4-phenyl-1-butyl. Preferred are the phenylmethyl, phenylethyl and phenylpropyl. Especially preferred are those having 1–2 carbon atoms in the alkyl chain.

When $R_1$ or $R_4$ is substituted phenyl or $R_4$ is substituted phenylalkyl, the phenyl group can be substituted by, e.g., 1, 2 or 3 groups such as, for example, 2-Cl, 3-Cl, 4-Cl, 4-Br, 4-F, 4-CH$_3$, 4-CH$_3$O, 2-NO$_2$, 4-NO$_2$, 3-CF$_3$, 2,4-dimethyl, 2,4-dichloro, 3,5-dimethyl, 2,4-dimethoxy, 3,4-dichloro, 2,6-dichloro, 3,5-di-NO$_2$ and 2,4,6-trimethyl.

Acids forming physiologically acceptable salts include both inorganic acids, e.g., hydrochloric acid, sulfuric acid, nitric acid or phosphoric acid, and organic acids, e.g., acetic acid, propionic acid, lactic acid, succinic acid, tartaric acid, citric acid, benzoic acid, salicylic acid, nicotinic acid and hept gluconic acid.

Preferred reactive ester groups are sulfonyloxy groups, e.g., methanesulfonyloxy, benzenesulfonyloxy, 4-toluenesulfonyloxy and bromosulfonyloxy.

The imidazole derivatives of general Formula I can be prepared according to reaction (a) as well as reaction (b). Those wherein X = NH preferably are produced according to (b).

The reaction of a compound of general Formula II with imidazole according to reaction (a) is conducted in a solvent, such as, for example, dimethylformamide, hexamethylphosphoric triamide, an aromatic hydrocarbon, e.g., benzene or toluene, an ether, e.g., diethyl ether, dioxane, tetrahydrofuran, or 1,2-dimethoxyethane, a lower alcohol or in water, at temperatures of from 0° C. to the boiling point of the solvent employed, preferably from 20° C. to the boiling point of the solvent employed or, in the absence of solvent, from 80° C. to 200° C., preferably 100° C. to 180° C., advantageously in the presence of a suitable catalyst, e.g., p-toluenesulfonic acid, pulverized copper, or an alkali iodide. The use of a catalyst can, in particular, also result in an improvement in the yield of the desired process products.

The imidazole can be utilized either in the free form or in the form of an alkali salt, which latter can be obtained from imidazole and an alkali hydride, alkali amide, alkali alcoholate or alkali hydroxide.

The reaction according to procedure (b) takes place in a conventional manner. The starting compounds can be used in the free form or as salts. Starting compounds wherein X is O or S, salts are preferably employed as the starting materials first forming the alkali salt of the compound of general Formula III with an alkali base, such as, for example, an alkali hydride, alkali amide, alkali alcoholate or alkali hydroxide. The starting compound is then reacted with a compound of general Formula IV in one of the above-mentioned solvents at temperatures of from 0° C. to the boiling point of the solvent utilized, preferably 20° C. to 70° C.

The starting compounds of general Formulae II and III are either known in the literature or can be prepared from known compounds according to analogous processes.

It has now been found that the novel compounds of general Formula I are valuable medicinal agents in human and veterinary medicine. They are highly effective with low toxicity against dermatophytes, e.g., *Trichophyton rubrum* and *Trichophyton mentagrophytes* and against yeasts, e.g., *Candida albicans*. They are also active against protozoa, especially trichomonads, as well as against gram-positive and gram-negative bacteria. The compounds also are effective in combating systemic fungal infections.

Table I illustrates the high activity of the compounds of this invention, using as examples the compounds numbered 5–25, which are compared to the known compounds 1–4, viz., the ethyl ester of 1-(1,2,3,4-tetrahydro-1-naphthyl)-imidazole-5-carboxylic acid (Etonam) and the commercially available 2-dimethylamino-6-($\beta$-diethylaminoethoxy)-benzothiazole, dihydrochloride (Dimazol dihydrochloride), as well as N-(2-hydroxybenzyl)-imidazole and N-(4-hydroxybenzyl)-imidazole (Bull. Soc. Chim. France 1973, 1179). The MIC values were determined by the tube test.

TABLE I

| | Compound | Minimum Inhibitory Concentration MIC in $\mu$./ml. Against | | |
| --- | --- | --- | --- | --- |
| | | Candida albicans | Trichophyton mentagrophytes | Trichophyton rubrum |
| (1) | Etonam [1-(1,2,3,4-Tetrahydro-1-naphthyl)-imidazole-5-carboxylic Acid Ethyl Ester] | inactive | 50 | 50 |
| (2) | Dimazole Dihydrochloride [2-Dimethylamino-6-($\beta$-diethylaminoethoxy)-benzothiazole, dihydrochloride] | inactive | inactive | inactive |
| (3) | N-(2-Hydroxybenzyl)-imidazole | inactive | inactive | >100 |
| (4) | N-(4-Hydroxybenzyl)-imidazole | inactive | inactive | inactive |
| (5) | (2,4-Dichlorobenzyl)-[3-(1-imidazolylmethyl)-phenyl]-ether | 25 | 1.6 | 0.8 |
| (6) | (2,4-Dichlorobenzyl)-[4-(1-imidazolylmethyl)-phenyl]-ether | 25 | 3.1 | 3.1 |
| (7) | (4-Chlorobenzyl)-[4-(1-imidazolylmethyl)-phenyl]-ether | 12.5 | 6.3 | 6.3 |
| (8) | (4-Bromobenzyl)-[4-(1-imidazolylmethyl)- | | | |

TABLE I-continued

| | Compound | Minimum Inhibitory Concentration MIC in μ./ml. Against | | |
|---|---|---|---|---|
| | | Candida albicans | Trichophyton mentagrophytes | Trichophyton rubrum |
| | phenyl]-ether | 6.3 | 1.6 | 0.8 |
| (9) | [4-Bromo-2-(1-imidazolylmethyl)-phenyl]-(2,4-dichlorobenzyl)-ethyl, Hydrochloride | 25 | 1.6 | 0.8 |
| (10) | N-(2,4-Dichlorobenzyl)-2-(1-imidazolylmethyl)-aniline | 12.5 | 0.8 | 0.4 |
| (11) | N-(2,4-Dichlorobenzyl)-4-(1-imidazolylmethyl)-aniline | 25 | 12.5 | 6.3 |
| (12) | (3,4-Dichloro-α-methylbenzyl)-[2-(1-imidazolylmethyl)-phenyl]-ether, Hydrochloride | 31 | 1 | 1 |
| (13) | (2,4-Dichlorobenzyl)-[2-(1-imidazolyl-phenyl]-ether, Hydrochloride | 31 | 4 | 4 |
| (14) | (3,4-Dichlorobenzyl)-[2-(1-imidazolyl)-4-methylphenyl]-ether, Sulfate | 50 | 1.6 | 6.3 |
| (15) | N-(2,4-Dichlorobenzyl)-4-(1-imidazolyl)-aniline, Hydrochloride, Dihydrate | 50 | 3.1 | 3.1 |
| (16) | (2,4-Dichlorobenzyl)-{4-[2-(1-imidazolyl)-ethyl]-phenyl}-ether, Hydrochloride | 6.3 | 0.4 | 0.4 |
| (17) | (2,4-Dichlorobenzyl)-{2-[2-(1-imidazolyl)-ethyl]-phenyl}-ether, Hydrochloride | 12.5 | 0.025 | 0.05 |
| (18) | (2,4-Dichlorobenzyl)-{2-[3-(1-imidazolyl)-1-propyl]-phenyl}-ether, Hydrochloride, Hydrate | 25 | 6.3 | 6.3 |
| (19) | (2,4-Dichlorobenzyl)-{2-[1-(1-imidazolyl)-butyl]-phenyl}-ether phenyl]-ether, Hydrochloride | 12.5 | 0.5 | 0.25 |
| (20) | (4-Chlorophenyl)-[2-(1-imidazolylmethyl)- | 50 | 6.3 | 6.3 |
| (21) | (4-Chlorophenyl)-[2-(1-imidazolylmethyl)-phenyl]-sulfide, Hydrochloride | 63 | 1.0 | 0.5 |
| (22) | (4-Chlorobenzyl)-[2-(1-imidazolylmethyl)-phenyl]-sulfide, Hydrochloride | 25 | 0.4 | 0.4 |
| (23) | (3,4-Dichlorobenzyl)-[2-(1-imidazolyl-methyl)-phenyl]-sulfide, Hydrochloride | 25 | 0.025 | 0.2 |
| (24) | (3-Chlorobenzyl)-{2-[1-(1-imidazolyl)-butyl]-phenyl}-ether, Hydrochloride | 6.3 | 0.2 | 0.1 |
| (25) | (Benzyl)-{4-[1-(1-imidazolyl)-butyl]-phenyl}-ether | 31 | 1 | 1 |

As can be seen from Table I, the reference compounds do not possess activity against *Candida albicans*. In contrast thereto, the compounds of this invention exhibit systemic activity.

The compounds of this invention can be administered in the pharmaceutically customary forms of application. The compounds are especially suitable for topical application, for example, in solutions, powders, creams, sprays and ointments. Suitable for oral administration are, e.g., tablets, dragees, capsules, pills and suspensions. Tablets can contain, for example, 0.05 to 0.50 g. of active agent and 0.1 to 5 g. of a pharmacologically indifferent auxiliary agent. Suitable auxiliary substances for tablets are, for example, lactose, amylose, talc, gelatin and magnesium stearate.

The novel compounds are customarily administered in amounts of from 0.1 to 4.0 g. per patient per day.

In the following examples, the temperatures are set forth in degrees Celsius.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

[4-(1-Imidazolylmethyl)-phenyl]-benzyl Ether 1.74 g. of 4-(1-imidazolylmethyl)-phenol (Bull. Soc. Chim. France 1973, 1179) is dissolved in 40 ml. of dimethylformamide and combined with 300 mg. of an 80% suspension of sodium hydride in oil. After 1.5 hours of agitation at room temperature, 1.27 g. of benzyl chloride is added thereto and the mixture stirred at room temperature for another 3 hours. Then, the mixture is poured on 100 ml. of 1N hydrochloric acid, extracted with ether, and the aqueous phase is made alkaline with sodium hydroxide solution. After extraction with methylene chloride, drying, and evaporation under vacuum, crystallization from cyclohexane/ether yields 2.3 g. of [4-(1-imidazolylmethyl)-phenyl]-benzyl ether, m.p. 94°–97°.

EXAMPLE 2

[4-(1-Imidazolylmethyl)-phenyl]-(2-nitrobenzyl)-ether, Hydrochloride

Analogously to Example 1, a crude ether is obtained from 1.74 g. of 4-(1-imidazolylmethyl)-phenol, 300 mg. of sodium hydride suspension, and 1.72 g. of 2-nitrobenzyl chloride. This crude ether is dissolved in methanol and combined with an excess of methanol which contains hydrogen chloride until the mixture shows an acidic reaction. After the solvent has been removed by evaporation under vacuum, the residue is dissolved in methylene chloride and mixed with ether until the onset of crystallization, thus obtaining 925 mg. of [4-(1-imidazolylmethyl)-phenyl]-(2-nitrobenzyl)-ether, hydrochloride, which melts at 156°–158° after another recrystallization from isopropanol.

EXAMPLE 3

[4-(1-Imidazolylmethyl)-phenyl]-(p-tolylmethyl)-ether

This compound is produced analogously to Example 1 from 4-(1-imidazolylmethyl)-phenol and 4-methylbenzyl chloride.

Yield: 66% of theory; m.p. 107°–111°.

EXAMPLE 4

[4-(1-Imidazolylmethyl)-phenyl]-(4-methoxybenzyl)-ether

This substance is prepared analogously to Example 1 from 4-(1-imidazolylmethyl)-phenol and 4-methoxybenzyl chloride.

Yield: 84% of theory; m.p. 113°–118°.

EXAMPLE 5

(4-Chlorobenzyl)-[4-(1-imidazolylmethyl)-phenyl]-ether

This compound is produced in analogy to Example 1 from 4-(1-imidazolylmethyl)-phenol and 4-chlorobenzyl chloride.

Yield: 74% of theory; m.p. 95°–97°.

EXAMPLE 6

(2,4-Dichlorobenzyl)-[4-(1-imidazolylmethyl)-phenyl]-ether

This substance is produced analogously to Example 1 from 4-(1-imidazolylmethyl)-phenol and 2,4-dichlorobenzyl chloride.

Yield: 85% of theory; m.p. 62°–64°.

EXAMPLE 7

(2,6-Dichlorobenzyl)-[4-(1-imidazolylmethyl)-phenyl]-ether, Hydrochloride

This compound is produced according to Example 2 from 4-(1-imidazolylmethyl)-phenol and 2,6-dichlorobenzyl chloride.

Yield: 75% of theory; m.p. 206°–209°.

EXAMPLE 8

(4-Bromobenzyl)-[4-(1-imidazolylmethyl)-phenyl]-ether

This substance is prepared analogously to Example 1 from 4-(1-imidazolylmethyl)-phenol and 4-bromobenzyl bromide.

Yield: 97% of theory; m.p. 108°–110°.

EXAMPLE 9

[4-(1-Imidazolylmethyl)-phenyl]-(2-propinyl)-ether

The above compound is prepared in analogy to Example 1 from 4-(1-imidazolylmethyl)-phenol and 1-bromo-2-propyne.

Yield: 90% of theory; m.p. 106°–108°.

EXAMPLE 10

[4-(1-Imidazolylmethyl)-phenyl]-(2-propenyl)-ether, Hydroperchlorate

This substance is produced analogously to Example 2 from 4-(1-imidazolylmethyl)-phenol and 1-bromo-2-propene with the use of perchloric acid.

Yield: 85% of theory; m.p. 87°–90°.

EXAMPLE 11

Ethyl-[4-(1-imidazolymethyl)-phenyl]-ether, Hydroperchlorate

This compound is prepared analogously to Example 2 from 4-(1-imidazolylmethyl)-phenol and ethyl iodide.

Melting point: 111°–116° (from methanol/ether).

EXAMPLE 12

Hexyl-[4-(1-imidazolylmethyl)-phenyl]-ether, Hydroperchlorate

This compound is prepared analogously to Example 2 from 4-(1-imidazolylmethyl)-phenol and hexyl iodide.

Melting point: 56°–57° (from ether/pentane).

EXAMPLE 13

[4-(1-Imidazolylmethyl)-phenyl]-(3-trifluoromethylbenzyl)-ether, Hydroperchlorate This substance is prepared in analogy to Example 2 from 4-(1-imidazolylmethyl)-phenol and 3-chloromethylbenzotrifluoride with the use of perchloric acid.

Yield: 58%; m.p. 87°–88°.

EXAMPLE 14

(2,4-Dichlorobenzyl)-[2-(1-imidazolylmethyl)-phenyl]-ether

Analogously to Example 1, 2.21 g. of (2,4-dichlorobenzyl)-[2-(1-imidazolymethyl)-phenyl]-ether, m.p. 108°–110°, is obtained from 1.74 g. of 2-(1-imidazolylmethyl)-phenol (Bull. Soc. Chim. France 1973, 1179), 300 mg. of sodium hydride suspension, and 1.41 g. of 2,4-dichlorobenzyl) chloride.

EXAMPLE 15

(2,4-Dichlorobenzyl)-[2-(1-imidazolylmethyl)phenyl]-sulfide, Hydrochloride 2.72 g. of imidazole in 50 ml. of dimethylformamide is combined with 1.2 g. of sodium hydride suspension (80% strength). After allowing the mixture to stand at room temperature for 1.5 hours, 12.7 g. of (2-chloromethylphenyl)-(2,4-dichlorobenzyl)-sulfide is added thereto (prepared analogously to J. Org. Chem. 30 [1965] 4074), and the mixture is agitated for 20 hours at room temperature. After working up the mixture as indicated in Example 2, 12.5 g. of (2,4-dichlorobenzyl)-[2-(1-imidazolylmethyl)-phenyl]-sulfide, hydrochloride, is obtained by recrystallization from methylene chloride, m.p. 171°–175°.

Analogously to Example 15, the following compounds are prepared:

(3,4-dichlorobenzyl)-{2-[1-(1-imidazolyl)-butyl]-phenyl}-sulfide (3-chlorobenzyl)-{2-[1-(1-imidazolyl)-butyl]-phenyl}-sulfide (3,4-dichlorobenzyl)-{2[1-(1-imidazolyl)-butyl]-4-methoxyphenyl}-sulfide (3-chlorobenzyl)-{2-[1-(1-imidazolyl)-butyl]-4-methoxyphenyl}-sulfide.

EXAMPLE 16

(2,4-Dichlorobenzyl)-[3-(1-imidazolylmethyl)-phenyl]-ether 15.2 g. of methyl 3-hydroxybenzoate in 100 ml. of dimethylformamide is combined with 3 g. of sodium hydride suspension (80%) and, after 2 hours of agitation at room temperature, with 19.5 g. of 2,4-dichlorobenzyl chloride. After 4 hours of stirring at room temperature, the mixture is introduced into 1N sulfuric acid, extracted with ether, and evaporated after drying, thus obtaining 28.2 g. of the methyl ester of 3-(2,4-dichlorobenzyloxy)-benzoic acid, m.p. 113°–114°. This product is reduced in ether with 1.52 g. of lithium aluminum hydride, yielding 21.4 g. of 3-(2,4-dichlorobenzyloxy)-benzyl alcohol, m.p. 93°94°. 2.83 g. of the alcohol is stirred with 15 ml. of thionyl chloride for 30 minutes at room temperature. After the thionyl chloride has been evaporated under vacuum, one obtains as the residue 2.16 g. of (3-chloromethyl-phenyl)-(2,4-dichlorobenzyl)-ether, m.p. 49°–52°. 1.9 g. of the halogenide is added to a mixture of 0.43 g. of imidazole and 200 mg. of sodium hydride suspension (80%) in 10 ml. of dimethylformamide, which was stirred for 2 hours at room temperature. After 3 hours of agitation at room temperature, the mixture is worked up as set forth in Example 1, yielding 1.18 g. of (2,4-dichlorobenzyl)-[3-(1-imidazolylmethyl)-phenyl]-ether, m.p. 79°–82°.

EXAMPLE 17

[4-Bromo-2-(1-imidazolylmethyl)-phenyl]-(2,4-dichlorobenzyl)-ether, Hydrochloride 3.74 g. of 5-bromosalicyl alcohol obtained by the reduction of 5-bromosalicylic acid with lithium aluminum hydride in ether, and 1.36 g. of imidazole are heated for 8 hours to 160°. After cooling, the melt is treated in methanol with active carbon. After evaporation of the solvent, 1.43 g. of 4-bromo-2-imidazolylmethylphenol, m.p. 163°–169° is obtained from methylene chloride/pentane. Reaction of 506 mg. of the phenol with 60 mg. of sodium hydride suspension (80%) and 392 mg. of 2,4-dichlorobenzyl chloride analogously to Example 2 yields 830 mg. of [4-bromo-2-(1-imidazolylmethyl)-phenyl]-(2,4-dichlorobenzyl)-ether, hydrochloride, m.p. 186°–190°.

The following compounds are prepared analogously to Example 17:
[4-chloro-2-(1-imidazolylmethyl)-phenyl]-(3,4-dichlorobenzyl)-ether and
(3,4-dichlorobenzyl)-[3,5-dichloro-2-(1-imidazolylmethyl)-phenyl]-ether.

EXAMPLE 18

[4-Chloro-2-(1-imidazolylmethyl)-phenyl]-(2,4-dichlorobenzyl)-ether

This compound is produced analogously to Example 17 from 5-chlorosalicylic acid and 2,4-dichlorobenzyl chloride.

Yield: 72%, based on the phenol; m.p. 133°–134°.

EXAMPLE 19

[4,6-Dibromo-2-(1-imidazolylmethyl)-phenyl]-(2,4-dichlorobenzyl)-ether, Hydrochloride This compound is prepared in analogy to Example 17 from 3,5-dibromosalicylic acid and 2,4-dichlorobenzyl chloride.

Yield: 36%, based on the phenol; m.p. 178°–180°.

EXAMPLE 20

(2,4-Dichlorobenzyl)-[2-(1-imidazolylmethyl)-4-methylphenyl]-ether

This substance is produced according to Example 17 from 5-methylsalicylic acid and 2,4-dichlorobenzyl chloride.

Melting point: 107°–109° (from benzene).

EXAMPLE 21

(2,4-Dichlorobenzyl)-[2-(1-imidazolylmethyl)-4-(1,1,3,3-tetramethylbutyl)-phenyl]-ether, Hydrochloride This compound is prepared analogously to Example 17 from 5-(1,1,3,3-tetramethylbutyl)-salicylic acid and 2,4-dichlorobenzyl chloride.

Melting point: 169°–173° (methylene chloride/ether).

EXAMPLE 22

(2,4-Dichlorobenzyl)-[4-(1-imidazolylmethyl)-2-methoxyphenyl]-ether

This substance is prepared according to Example 17 from 4-hydroxy-3-methoxybenzoic acid and 2,4-dichlorobenzyl chloride. The product was recrystallized from ethanol/water. Yield: 70%, based on the phenol; m.p. 68°–69°.

EXAMPLE 23

(2,4-Dichlorobenzyl)-[2-(1-imidazolylmethyl)-4-methylthiophenyl]-ether

This substance is produced analogously to Example 17 from 5-methylthiosalicylic acid and 2,4-dichlorobenzyl chloride.

Melting point: 90°–93° (methylene chloride/ether).

EXAMPLE 24

(2,4-Dichlorobenzyl)-[3-(1-imidazolylmethyl)-2-naphthyl]-ether

This compound is produced analogously to Example 17 from 2-hydroxy-3-naphthoic acid and 2,4-dichlorobenzyl chloride.

Melting point: 164°–165° (benzene/cyclohexane).

EXAMPLE 25

[4-(1-Imidazolylmethyl)-2-nitrophenyl]-(2,4-dichlorobenzyl)-ether 5.5 g. of 4-hydroxy-3-nitrobenzaldehyde is reacted with 6.7 g. of 2,4-dichlorobenzyl chloride analogously to Chem. Abstr. 71 (1969) 30232, thus obtaining 5.2 g. of 4-(2,4-dichlorobenzyloxy)-3-nitrobenzaldehyde, m.p. 172°–174°. Of this product, 0.9 g. is dissolved in methanol/dioxane and reduced with 500 mg. of sodium borohydride, yielding 580 mg. of 4-(2,4-dichlorobenzyloxy)-3-nitrobenzyl alcohol, m.p. 126°–127°. 450 mg. of this product is heated with 5 ml. of thionyl chloride for 5 minutes to 100°. After the residual thionyl chloride has been removed under vacuum, the remainder is vacuum-filtered with ethanol, thus producing 400 mg. of (4-chloromethyl-2-nitrophenyl)-(2,4-dichlorobenzyl)-ether, m.p. 147°–149°. 300 mg. of this ether is added to a solution of 68 mg. of imidazole in 3 ml. of dimethylformamide, which was agitated with the addition of 30 mg. of sodium hydride suspension (80%) for 1 hour at room temperature, and the mixture is stirred for another hour at room temperature. Then, the mixture is combined with 1N sulfuric acid and the thus-precipitated product is vacuum-filtered, dissolved in methanol/chloroform, and extracted with 1N sodium hydroxide solution. The chloroform phase is washed with water, dried, and evaporated. Recrystallization from cyclohexane/benzene yields 260 mg. of [4-(4-(1-imidazolylmethyl)-2-nitrophenyl]-(2,4-dichlorobenzyl)-ether, m.p. 120°–124°.

EXAMPLE 26

(2,4-Dichlorobenzyl)-{4[α-(1-imidazolyl)-benzyl]-phenyl}-ether, Hydroperchlorate 19.8 g. of 4-hydroxybenzophenone is agitated in 100 ml. of dimethylformamide with 3.0 g. of sodium hydride suspension (80%) for 1 hour; thereafter, 20.5 g. of 2,4-dichlorobenzyl chloride is added. After standing for 1 hour at room temperature, the mixture is added to 1N hydrochloric acid, extracted with ethyl acetate, and drying, evaporation, and recrystallization from ethanol yield 24 g. of 4-(2,4-dichlorobenzyloxy)-benzophenone, m.p. 87° C. Of this product, 10 g. is dissolved in 50 ml. of tetrahydrofuran and 50 ml. of methanol and agitated with 1.5 g. of sodium borohydride for 1 hour. The mixture is then poured on 1N sulfuric acid and extracted with methylene chloride. After drying of the organic phase, the solvent is carefully removed under vacuum and the residue recrystallized from ethanol, thus obtaining 6 g. of 4-(2,4-dichlorobenzyloxy)-benzohydrol, m.p. 89°–90° C.

One gram of this last-mentioned product is heated with 500 mg. of imidazole and 500 mg. of p-toluenesulfonic acid for 30 minutes to 180°. After cooling, the mixture is dissolved in chloroform, extracted with potassium carbonate solution, double the volume of ether is added to the organic phase, the latter is extracted with 2N hydrochloric acid, and the aqueous phase is rendered alkaline with sodium hydroxide solution. The reaction mixture is extracted with methylene chloride. The residue remaining after drying and evaporation of the organic phase is dissolved in ether and combined with methanolic perchloric acid until the mixture shows a weakly acidic reaction. The oil remaining after evaporation of the solvent is crystallized from ethyl acetate/ether, thus obtaining 880 mg. of (2,4-dichlorobenzyl)-{4-[α-(1-imidazolyl)-benzyl]-phenyl}-ether, hydroperchlorate, m.p. 106°–113°.

EXAMPLE 27

(2,4-Dichlorobenzyl)-{4-[α-(1-imidazolyl)-4-methylbenzyl]-phenyl}-ether

This compound is produced analogously to Example 26 from 4-hydroxy-4'-methylbenzophenone.

EXAMPLE 28

(2,4-Dichlorobenzyl)-{2-[2,4-dimethoxy-α-(1-imidazolyl)-benzyl]-5-methoxyphenyl}-ether This substance is prepared according to Example 26 from 2-hydroxy-2',4,4'-trimethoxybenzophenone, the latter having been obtained by reacting 2,2'-dihydroxy-4,4'-dimethoxybenzophenone with an equivalent of diazomethane.

EXAMPLE 29

{2-[4-Chloro-α-(1-imidazolyl)-benzyl]-5-methoxyphenyl}-(2,4-dichlorobenzyl)-ether This compound is prepared analogously to Example 26 from 4'-chloro-2-hydroxy-4-methoxybenzophenone.

EXAMPLE 30

(2,4-Dichlorobenzyl)-{4-[α-(1-imidazolyl)-4-nitrobenzyl]-phenyl}-ether

This substance is produced according to Example 26 from 4-hydroxy-4'-nitrobenzophenone (Chem. Abstr. 55 [1961] 22217).

EXAMPLE 31

(2,4-Dichlorobenzyl)-{4-[1-(1-imidazolyl)-ethyl]-phenyl}-ether, Hydroperchlorate 136 g. of 4-hydroxyacetophenone is etherified in 500 ml. of dimethylformamide with 30 g. of sodium hydride oil suspension (80%) and 195 g. of 2,4-dichlorobenzyl chloride analogously to Example 16. The thus-obtained 4-(2,4-dichlorobenzyloxy)-acetophenone (290 g., m.p. 89°–90°) is reduced in 1 liter of ethanol/dioxane (2 : 1) with 50 g. of sodium borohydride analogously to Example 26, and worked up. Of the thusobtained 4-(2,4-dichlorobenzyloxy)-α-methylbenzyl alcohol (m.p. 61°–64°), 1.7 g. is stirred with 5 ml. of thionyl chloride for 1 hour at room temperature. The product remaining after a careful evaporation of the thionyl chloride is reacted according to Example 15 with a solution of sodium imidazole, prepared from 360 mg. of imidazole and 160 mg. of sodium hydride, and converted into the perchlorate as described in Example 26. Yield: 940 mg.; m.p. 103°–106° (methylene chloride/ether).

EXAMPLE 32

(2,4-Dichlorobenzyl)-{2-[1-(1-imidazolyl)-butyl]-phenyl}-ether

This compound is prepared analogously to Example 31 from 2-hydroxybutyrophenone; m.p. 89°–90° (ether).

The following compounds are produced analogously to Example 32:

(3-chlorobenzyl)-{2-[1-(1-imidazolyl)-proplyl]-phenyl}-ether (3,4-dichlorobenzyl)-{2-[1-(1-imidazolyl)-propyl]-phenyl}-ether (3-chlorobenzyl)-{2-[1-(1-imidazolyl)-2-methylpropyl]-phenyl}-ether (3,4-dichlorobenzyl)-{2-[1-(1-imidazolyl)-2-methylpropyl]-phenyl}-ether (3,4-dichlorobenzyl)-{2-[1-(1-imidazolyl)-pentyl]-phenyl}-ether (3-chloro-α-methylbenzyl)-{2-[1-(1-imidazolyl)-butyl]-phenyl}-ether (3,4-dichloro-α-methylbenzyl)-{2[1-imidazolyl)-butyl]-phenyl}-ether
(3-chlorobenzyl)-{5-chloro-2-[1-(1-imidazolyl)-butyl]-phenyl}-ether
{5-chloro-2-[1-(1-imidazolyl)-butyl]-phenyl}-(3,4-dichlorobenzyl)-ether
(3-chlorobenzyl)-{4-chloro-2-[1-(1-imidazolyl)-butyl]-phenyl}-ether
{4-chloro-2-[1-(1-imidazolyl)-butyl]-phenyl}-(3,4-dichlorobenzyl)-ether
{4-chloro-2-[1-(1-imidazolyl)-butyl]-phenyl}-(2,4-dichlorobenzyl)-ether
(3-chlorobenzyl)-{2-[1-(1-imidazolyl)-ethyl]-phenyl}-ether
(3,4-dichlorobenzyl)-{2-[1-(1-imidazolyl)-ethyl]-phenyl}-ether
(3-chlorobenzyl)-{3,5-dichloro-2-[1-(1-imidazolyl)-butyl]-phenyl}-ether
(2,4-dichlorobenzyl)-{3,5-dichloro-2-[1-(1-imidazolyl)-butyl]-phenyl}-ether
(3,4-dichlorobenzyl)-{3,5-dichloro-2-[1-(1-imidazolyl)-butyl]-phenyl}-ether
(3-chlorobenzyl)-{4,5-dichloro-2-[1-(1-imidazolyl)-butyl]-phenyl}-ether
(2,4-dichlorobenzyl)-{4,5-dichloro-2-]1-(1-imidazolyl)-butyl]-phenyl}-ether
(3,4-dichlorobenzyl)-{4,5-dichloro-2-[1-(1-imidazolyl)-butyl]-phenyl}-ether.

EXAMPLE 33

{4-Chloro-2-[α-(1-imidazolyl)-benzyl]-phenyl}-(2,4-dichlorobenzyl)-ether 23 g. of 5-chloro-2-hydroxybenzophenone is reduced with an excess of sodium borohydride in methanol, thus obtaining 10.5 g. of 5-chloro-2-hydroxybenzohydrol, m.p. 132°–134° (from benzene). 2.3 g. of this product is heated with 670 mg. of imidazole for 2.5 hours to 200°. The reaction mixture is then dissolved in ethanol, a small amount of water is added, and this yields 500 mg. of 4-chloro-2-[α-(1-imidazolyl)-benzyl]-phenol, m.p. 228°–232°. The product is stirred in 7.5 ml. of dimethylformamide with 65 mg. of sodium hydride suspension (80%) for 1.5 hours at room temperature and then combined with 440 mg. of 2,4-dichlorobenzyl chloride. After the mixture has been worked up as set forth in Example 1, it is recrystallized from benzene/cyclohexane, thus obtaining 430 mg. of {4-chloro-2-[α-(1-imidazolyl)-benzyl[-phenyl}-(2,4-dichlorobenzyl)-ether, m.p. 115°–120°.

EXAMPLE 34

2-(1-Imidazolylmethyl)-diphenyl Ether, Hydrochloride 816 mg. of imidazole is stirred in 8 ml. of dimethylformamide with 360 mg. of sodium hydride suspension (80%) for 1.5 hours. Then, 2.6 g. of 2-chloromethyl-diphenyl ether (Coll. Czech. Chem. Commun. 34 [1969]2258) is added thereto. After 20 hours of agitation at room temperature the mixture is worked up analogously to Example 2, thus obtaining 320 mg. of 2-(1-imidazolylmethyl)-diphenyl ether, hydrochloride, m.p. 144°–145°.

EXAMPLE 35

4-Chloro-2'-(1-imidazolylmethyl)-diphenyl Ether, Hydrochloride

This compound is produced analogously to Example 34 from 4-chloro-2'-chloromethyldiphenyl ether (Coll. Czech. Chem. Commun. 34 [1969] 2258).
Yield: 31%; m.p. 94°–96°.

EXAMPLE 36

4-Chloro-2'-(1-imidazolylmethyl)-diphenyl Sulfide, Hydrochloride

This compound is produced analogously to Example 34 from 4-chloro-2'-chloromethyldiphenyl sulfide (Coll. Czech. Chem. Commun. 33 [1968] 1831).
Yield: 21%; m.p. 97°–98°.

EXAMPLE 37

(4-Bromobenzyl)-[4-bromo-2-(1-imidazolylmethyl)-phenyl]-ether, Hydrochloride

This substance is prepared analogously to Example 17 with the use of 4-bromobenzyl bromide.
Melting point: 221°–226° (from ethanol/ether).

EXAMPLE 38

(2,4-Dichlorobenzyl)-[4-chloro-2-(1-imidazolylmethyl)-phenyl]-ether

This compound is prepared from 5-chlorosalicylic acid analogously to Example 17.
Melting point: 133°–134° (from benzene/cyclohexane).

EXAMPLE 39

[5-Bromo-2-(1-imidazolylmethyl)-phenyl]-(2,4-dichlorobenzyl)-ether

This compound is prepared analogously to Example 17 from 4-bromosalicylic acid (Chem. Abstr. 59 [1963] 3925g).
Melting point: 120°–122° (from methylene chloride/ether).

EXAMPLE 40

(2,4-Dichlorobenzyl)-{2-[1-(1-imidazolyl)-butyl-phenyl}-ether, Nitrate

This product is obtained from the compound described in Example 32 with nitric acid.
Melting point: 111°–112° (from water).

EXAMPLE 41

(3-Chlorobenzyl)-{2-[1-(1-imidazolyl)-butyl]-phenyl}-ether, Hydrochloride

Analogously to Example 32, this substance is prepared with the use of 3-chlorobenzyl chloride.
Melting point: 111°–113° (from ethyl acetate).

EXAMPLE 42

(3,4-Dichlorobenzyl)-{2-[1-(1-imidazolyl)-butyl]-phenyl}-ether, Hydrochloride

This compound is prepared according to Example 32 with the use of 3,4-dichlorobenzyl chloride.
Melting point: 149°–150° (from ethyl acetate).

EXAMPLE 43

(4-Bromobenzyl)-{2-[1-(1-imidazolyl)-butyl]-phenyl}-ether, Hydrochloride

This substance is prepared analogously to Example 32 with the use of 4-bromobenzyl bromide.
Melting point: 129°–131°(from benzene).

EXAMPLE 44

(2,4-Dichlorobenzl)-{2-[1-(1-imidazolyl)-heptyl]-phenyl}-ether, Hydrochloride

By etherifying salicylaldehyde with 2,4-dichlorobenzyl chloride in the usual manner, 2-(2,4-dichlorobenzyloxy)-benzaldehyde, m.p. 130°–131°, is obtained which is converted according to standard methods with hexylmagnesium iodide into 1-[2-(2,4-dichlorobenzyloxy)-phenyl]-heptanol. By treatment with thionyl chloride and then with sodium imidazole analogously to Example 16, and by conversion into the hydrochloride, the final product is obtained.
Melting point: 124°–126° (from methylene chloride/ether).

EXAMPLE 45

(2,4-Dichlorobenzyl)-{2-[1-(1-imidazolyl)-ethyl]-phenyl}-ether

This compound is produced analogously to Example 44 with the use of methylmagnesium bromide.
Melting point: 76°–80° (from ether/cyclohexane).

EXAMPLE 46

Benzyl-{4-[1-(1-imidazolyl)-butyl]-phenyl}-ether

This compound is prepared according to Example 31 with the use of 4-hydroxybutyrophenone and benzyl chloride.
Melting point: 91°–92° (from ether).

EXAMPLE 47

(3,4-Dichlorobenzyl)-[4-(1-imidazolylmethyl)-phenyl]-ether, Hydrochloride

This compound is prepared analogously to Example 2 with 3,4-dichlorobenzyl chloride.
Melting point: 110°–111° (from methylene chloride/ether).

EXAMPLE 48

(2,4-Dichlorobenzyl)-[2,6-dichloro-4-(1-imidazolylmethyl)-phenyl]-ether

This compound is produced according to Example 17 from 3,5-dichloro-4-hydroxybenzoic acid.
Melting point: 110°–111° (from benzene/ether).

EXAMPLE 49

Benzyl-[2-(1-imidazolylmethyl)-phenyl]-sulfide, Hydrochloride

This compound is prepared analogously to Example 15 with the use of benzyl chloride.
Melting point: 127°–129° (from acetonitrile).

EXAMPLE 50

(4-Chlorobenzyl)-[2-(1-imidazolylmethyl)-phenyl]-sulfide, Hydrochloride

This substance is produced in accordance with Example 15, using 4-chlorobenzyl chloride.
Melting point: 130°–132° (from acetonitrile).

EXAMPLE 51

(3-Chlorobenzyl)-[2-(1-imidazolylmethyl)-phenyl]-sulfide, Hydrochloride

This compound is prepared analogously to Example 15 with the use of 3-chlorobenzyl chloride.
Melting point: 172°–176° (from ethanol).

EXAMPLE 52

(3,4-Dichlorobenzyl)-[2-(1-imidazolylmethyl)-phenyl]-sulfide, Hydrochloride

Analogously to Example 15, this substance is prepared with the use of 3,4-dichlorobenzyl chloride.
Melting point: 135°–138° (from methylene chloride/ether).

EXAMPLE 53

N-(2,4-Dichlorobenzyl)-2-(1-imidazolylmethyl)-aniline 6.9 g. of imidazole is dissolved in 100 ml. of dimethylformamide and combined with 3 g. of an 80% strength sodium hydride-oil suspension. After 30 minutes of agitation at room temperature, 17.1 g. of 2-nitrobenzyl chloride is added, dissolved in 50 ml. of dimethylformamide, and the solution is stirred for one hour at room temperature. Then, the mixture is poured into 500 ml. of 1N hydrochloric acid, filtered, the clear solution is extracted with ether, and then the aqueous phase is made alkaline with 40% strength sodium hydroxide solution. The mixture is extracted with methylene chloride, the organic phase is dried, and evaporation of the solvent yields a crude product which is purified by twice conducting a vacuum distillation at 100°–110° (air bath temperature)/0.03 torr [mm. Hg] with the use of a bulb tube; m.p. 80°–82°; yield: 12.6 g. of 1-(2-nitrobenzyl)-imidazole.

This product is dissolved at 100° in 50 ml. of concentrated hydrochloric acid, then combined with 60 g. of tin (II) chloride dihydrate, dissolved in 50 ml. of concentrated hydrochloric acid, and heated at 100° until the solution is clear. After cooling, the reaction mixture is poured into a solution of 200 g. of sodium hydroxide in 500 ml. of water in a gradual stream, and then the mixture is extracted with methylene chloride. After distillation with the use of a bulb tube (120°–130°/0.03 torr), 9 g. of 2-(1-imidazolylmethyl)-aniline is obtained. The product is dissolved in 100 ml. of dimethylformamide and mixed with 10 g. of 2,4-dichlorobenzyl chloride. After 20 hours of agitation at room temperature, the mixture is poured on 300 ml. of 1N hydrochloric acid, extracted with ether, the aqueous phase made alkaline with sodium hydroxide solution, and extracted with chloroform. After drying and evaporation of the organic phase, a crude product is obtained which yields, after recrystallization from benzene, 8.5 g. of N-(2,4-dichlorobenzyl)-2-(1-imidazolylmethyl)-aniline, m.p. 149°–151°.

EXAMPLE 54

N-(2,4-Dichlorobenzyl)-4-(1-imidazolylmethyl)-aniline

This compound is prepared analogously to Example 53 from 4-nitrobenzyl chloride.
Melting point: 117°–118° (from methylene chloride/ether).

EXAMPLE 55

(3,4-Dichloro-α-methylbenzyl)-[2-(1-imidazolylmethyl)-phenyl]-ether, Hydrochloride This compound is produced analogously to Example 14 from 2-(1-imidazolylmethyl)-phenol and 1-chloro-1-(3,4-dichlorophenyl)-ethane, which latter was prepared as usual by sodium borohydride reduction of 3,4-dichloroacetophenone and subsequent treatment with thionyl chloride. The hydrochloride is formed analogously to Example 2.

Melting point 140°–143°.

EXAMPLE 56

Allyl-[2-(1-imidazolyl)-phenyl]-ether, Hydrochloride 1.6 g. of 2-(1-imidazolyl)-phenol [Khim. Geterotsikl. Soedin Akad. Nauk Latv. SSR 1966, 143; Chem. Abstr. 65 (1966) 13686] is dissolved in 20 ml. of dimethylformamide and combined with 300 mg. of a sodium hydride - oil suspension (80%). The mixture is agitated for one hour at room temperature, and then 760 mg. of allyl chloride is added thereto. After three hours of agitation at room temperature, the solution is added to 100 ml. of 1N sulfuric acid and extracted with ether. The aqueous phase is rendered alkaline with 40% sodium hydroxide solution and extracted with methylene chloride. After drying and evaporation of the solvent, the crude product is dissolved in a small amount of methanol and combined with methanolic hydrochloric acid until a weakly acidic reaction is observed. After the solvent has been evaporated under vacuum, the residue is dissolved in methylene chloride and mixed with ether until the onset of crystallization.

Yield: 940 mg., m.p. 159°–161°.

EXAMPLE 57

[2-(1-Imidazolyl)-phenyl]-(2-propinyl)-ether

Analogously to Example 56, this compound is prepared with the use of 1.19 g. of 3-bromopropyne. However, the crude product was distilled in a bulb tube at 60° (air bath temperature) and under 0.04 torr, and then recrystallized from ether.

Yield: 260 mg., m.p. 59°–61°.

EXAMPLE 58

[2-(1-Imidazolyl)-phenyl]-(4-methylbenzyl)-ether

This compound is produced analogously to Example 57 using 1.4 g. of 4-methylbenzyl chloride. The crude product is recrystallized from ether.

Yield: 1.52 g.; m.p. 76°–77°.

EXAMPLE 59

[2-(1-Imidazolyl)-phenyl]-(4-methoxybenzyl)-ether

Analogously to Example 57, this compound is produced with the use of 1.66 g. of 4-methoxybenzyl chloride.

Yield: 1.8 g.; m.p. 74°–75° (from cyclohexane).

EXAMPLE 60

(2,4-Dichlorobenzyl)-[2-(1-imidazolyl)-phenyl]-ether, Hydrochloride

This compound is produced analogously to Example 56 using 1.95 g. of 2,4-dichlorobenzyl chloride.

Yield: 2.6 g.; m.p. 171°–179°.

EXAMPLE 61

[2,4-Dichlorobenzyl)-[4-(1-imidazolyl)-phenyl]-ether, Hydrochloride

This substance is prepared from 1.6 g. of 4-(1-imidazolyl)-phenol [Khim. Geterotsikl. Soedin Akad. Nauk Latv. SSR 1966, 143; C.A. 65 (1966) 13686] and 1.95 g. of 2,4-dichlorobenzyl chloride, analogously to Example 56.

Yield: 3.2 g.; m.p. 217°–219°.

EXAMPLE 62

[2-(1-Imidazolyl)-phenyl]-2-nitrobenzyl Ether

Analogously to Example 57, this compound is produced with the use of 1.57 g. of 2-nitrobenzyl chloride.

Yield: 430 mg.; m.p. 112°–114° (from ethanol).

EXAMPLE 63

[2-(1Imidazoly)-phenyl]-[3-trifluoromethyl)-benzyl]-ether, Hydrochloride

This substance is produced analogously to Example 56 with the use of 1.95 g. of 3-(trifluoromethyl)-benzyl chloride.

Yield: 1.3 g.; m.p. 158°–162° (from methylene chloride/ether).

EXAMPLE 64

(3,4-Dichlorobenzyl)-[2-(1-imidazolyl)-4-methylphenyl]-ether, Sulfate 25 g. of 2-bromo-4-methylphenol is etherified with 17.4 g. of dimethyl sulfate in 70 ml. of 2N sodium hydroxide, and the methyl ether (18.7 g.) is reacted with imidazole (6.96 g.) analogously to the literature citation in Example 56. The methyl ether is subsequently cleaved (yield: 6.15 g.). One gram of the thus-obtained 2-(1-imidazolyl)-4-methylphenol is reacted according to Example 56, using 1.12 g. of 3,4-dichlorobenzyl chloride. After pouring the reaction mixture into 1N sulfuric acid, the product is obtained in crystalline form.

Yield: 2.3 g.; m.p. 208°–214°.

EXAMPLE 65

(2,4-Dichlorobenzyl)-[2-(1-imidazolyl)-4-nitrophenyl]-ether 2.15 g. of 1-(2-methoxyphenyl)-imidazole (literature citation in Example 56) is nitrated in a mixture of 60 ml. of acetic anhydride and 20 ml. of 65% nitric acid for 2 hours at 10°. By ether splitting (literature citation in Example 56) of the thus-formed 1-(2-methoxy-5-nitrophenyl)-imidazole (1.8 g.; m.p. 139°–140° from methylene chloride/ether), 420 mg. of 2-(1-imidazolyl)-4-nitrophenol is obtained according to the literature citation in Example 56. This product is etherified analogously to Example 56 with the use of 400 mg. of 2,4-dichlorobenzyl chloride.

Yield: 150 mg.; m.p. 182°–185° (from ethanol).

EXAMPLE 66

[4-Chloro-2-(1-imidazolyl)-phenyl]-(2,4-dichlorbenzyl)-ether 1.1 g. of the 1-(2-methoxy-5-nitrophenyl)-imidazole obtained in Example 65 is reduced by heating for 5 minutes with 3.75 g. of tin(II) chloride in 20 ml. of concentrated hydrochloric acid. The thus-formed 3-(1- imidazolyl)-4-methoxyaniline (830 mg.) is converted according to Sandmeyer in the usual way into the 1-(5-chloro-2-methoxyphenyl)-imidazole (610 mg.; m.p. 52°–57°). After ether cleavage according to the literature citation in Example 56, 4-chloro-2-(1-imidazolyl)-phenol is obtained (425 mg.), which is etherified analogously to Example 58 with the use of 4 25 mg. of 2,4-dichlorobenzyl chloride.

Yield: 540 mg.; m.p. 97°–98° (from cyclohexane).

The following compounds are prepared analogously to Example 66:

[4-chloro-2-(1-imidazolyl)-phenyl]-3,4-dichlorobenzyl)-ether

[5-chloro-2-(1-imidazolyl)-phenyl]-(3,4-dichlorbenyzl)-ether

[4-chloro-2-(1-imidazolyl)-phenyl]-(3,4-dichloro-α-methyl-benzyl)-ether (3,4-dichlorobenzyl)-[3,5-dichloro-2-(1-imidazolyl)-phenyl]-ether.

EXAMPLE 67

N-(2,4-Dichlorobenzyl)-2-(1-imidazolyl)-aniline

Three grams of 1-(2-nitrophenyl)-imidazole (J. Chem. Soc. C 1970, 85) is reduced with 18 g. of tin(II) chloride in 10 ml. of concentrated hydrochloric acid, yielding the 2-(1-imidazolyl)-aniline (1.97 g.; m.p. 100°–103° from benzene/cyclohexane). Of this compound, 1.59 g. is stirred with 1.95 g. of 2,4-dichlorobenzyl chloride in 20 ml. of dimethylformamide for 20 hours at room temperature and worked up analogously to Example 56.

Yield: 2 g.; m.p. 149°–155° (from ethanol).

EXAMPLE 68

N-(2,4-Dichlorobenzyl)-4-(1-imidazolyl)-aniline, Hydrochloride, Dihydrate

Analogously to Example 67, 13.8 g. of 4-(1-imidazolyl-aniline, m.p. 141°–142°, is obtained from 17.6 g. of 1-(4-nitrophenyl)-imidazole (J. Chem. Soc. C. 1970, 85). 1.59 g. of this product is reacted analogously to Example 67. The crude product obtained during the working-up step is converted according to Example 56 into the monohydrochloride, which is crystallized from water as the dihydrate.

Yield: 1.8 g.; m.p. 162°–167°.

EXAMPLE 69

4-(1-Imidazolyl)-diphenyl Ether, Hydrochloride 25 g. of 4-bromodiphenyl ether, 6.8 g. of imidazole, 13.8 g. of potassium carbonate, and 1 g. of pulverized copper are heated to 200° for 2 hours. After cooling, the reaction mixture is taken up in 2N hydrochloric acid, combined with ether, and the thus-precipitated crystals are filtered out. After recrystallization from methylene chloride/ether and subsequently from water, the pure product is obtained.

Yield: 15 g.; m.p. 174°–177°.

EXAMPLE 70

(2,4-Dichlorbenzyl)-[4-(1-imidazolyl)-phenyl]-sulfide 1.06 g. of 4-(1-imidazolyl)-aniline (see Example 68) is dissolved in 20 ml. of water and 0.8 of concentrated sulfuric acid and gradually combined at 15° with a solution of 0.5 g. of sodium nitrite in 2 ml. of water. The mixture is stirred for another 30 minutes and then gradually introduced underneath the surface of a solution of 1.5 g. of potassium ethylxanthate in 5 ml. of water, warmed to 70°–75°. After heating the mixture for another 2 hours to 90°, 1.06 g. of sodium hydroxide is added thereto. The mixture is then refluxed for 90 minutes and allowed to stand for 20 hours at room temperature; then, the mixture is neutralized with 2N hydrochloric acid and extracted with methylene chloride. The crude 4-(1-imidazolyl)-thiophenol obtained after drying and evaporation of the solvent is dissolved in 20 ml. of dimethylformamide and combined with 200 mg. of an 80% strength sodium hydride - oil suspension and, after 30 minutes stirring with 1.3 g. of 2,4-dichlorobenzyl chloride. After 3 hours of agitation at room temperature, the reaction mixture is worked up analogously to Example 56, and the crude product is chromatographed on 100 g. of silica gel. With chloroform/isopropanol (8 : 2), the desired product is eluted as a slightly yellow oil.

| Analysis: | C | H | Cl | S |
|---|---|---|---|---|
| Calculated | 57.30 | 3.58 | 21.20 | 9.55 |
| Found | 57.90 | 4.05 | 21.50 | 10.05 |

EXAMPLE 71

(2,4-Dichlorobenzyl)-[2-(1-imidazolyl-phenyl]-phenyl]-sulfide 1.6 g. of 2-(1-imidazolyl)-phenol (see Example 56) is reacted with 300 mg. of a sodium hydride - oil suspension (80%) in 20 ml. of dimethylformamide and then with 1.6 g. of dimethyl thiocarbamoyl chloride to obtain the dimethyl thiocarbamate in accordance with J. Org. Chem. 31 (1966) 3980. The product is rearranged in accordance with the above-indicated literature and then saponified, yielding 0.5 g. of 2-(1-imidazolyl)-thiophenol. 400 mg. of this product is reacted in 5 ml. of dimethylformamide with 68 mg. of sodium hydride - oil suspension (80%) and 450 mg. of 2,4-dichlorobenzyl chloride analogously to Example 70 and thereafter chromatographed, thus obtaining the desired product (250 mg.) as a light-yellow oil.

| Analysis: | C | H | Cl | S |
|---|---|---|---|---|
| Calculated | 57.30 | 3.58 | 21.20 | 9.55 |
| Found | 56.85 | 3.92 | 21.35 | 9.12 |

Analogously to Example 71, the following compounds are produced:

(3-chlorobenzyl)-[2-(1-imidazolyl)-phenyl]-sulfide
(3,4-dichlorobenzyl)-[2-(1-imidazolyl)-phenyl]-sulfide
(3,4-dichlorophenyl)-[2-(1-imidazolyl)-phenyl]-sulfide
(3,4-dichloro-α-methylbenzyl)-[2-(1-imidazolyl)-phenyl]-sulfide.

EXAMPLE 72

(2,4-Dichlorobenzyl)-{4-[2-(1-imidazolyl)-ethyl]-phenyl}-ether, Hydrochloride 2.8 g. of sodium hydroxide in 10 ml. of water and 13.6 g. of 2,4-dichlorobenzyl alcohol are added to 8 g. of 4-hydroxyphenethyl alcohol in 80 ml. of ethanol. After refluxing the solution for 1.5 hours, the mixture is acidified with dilute sulfuric acid and extracted with methylene chloride. Drying and evaporation of the solvent yields the crude product at 100°–130° (air bath temperature)//0.02 torr by distillation with the use of a bulb tube. From cyclohexane, 14.5 g. of 4-(2,4-dichlorobenzyloxy)-phenethyl alcohol is obtained, m.p. 55°. The alcohol is converted, by 10 minutes of heating with thionyl chloride, into the [4-(β-chloroethyl)-phenyl]-(2,4-dichlorobenzyl)-ether and added to a solution of sodium imidazole, obtained by reacting 2 g. of imidazole with 1.04 g. of 80% strength sodium hydride - oil suspension in 30 ml. of dimethylformamide; the mixture is agitated for 6 hours at 100°–120°. The product is worked up as indicated in Example 56.

Yield: 3.6 g.; m.p. 177°–185°.

EXAMPLE 73

(2,4-Dichlorobenzyl)-{2-[2-(1-imidazolyl)-ethyl]-phenyl}-ether, Hydrochloride

Analogously to Example 72, the above product is obtained from 16.6 g. of 2-hydroxyphenethyl alcohol.

Yield: 5 g.; m.p. 140°–145° (from methylene chloride/ether).

Analogously to Example 73, the following compounds are prepared:
(2,4-dichlorobenzyl)-{2-[1-ethyl-2-(1-imidazolyl)-ethyl]-phenyl}-ether
(3,4-dichlorobenzyl)-{2-[1-ethyl-2-(1-imidazolyl)-ethyl]-phenyl}-ether
(2,4-dichlorobenzyl)-{2-[2-(1-imidazolyl)-1-propylethyl]-phenyl}-ether
(3,4-dichlorobenzyl)-{2-[2-(1-imidazolyl)-1-propylethyl]-phenyl}-ether.

EXAMPLE 74

(2,4-Dichlorobenzyl)-{2-[3-(1-imidazolyl)-propyl]-phenyl}-ether, Hydrochloride, Hydrate This product is obtained analogously to Example 72 from 39 g. of 3-(2-hydroxyphenyl)-propyl alcohol (Helv. Chim. Acta 32 [1949] 1962).

Yield: 13 g.; m.p. 138°–140° (from ethyl acetate).

EXAMPLE 75

{4-[3-(1-Imidazolyl)-1-methylpropyl]-phenyl}-(4-methylbenzyl)-ether, Hydrochloride 100 g. of 4-methoxyacetophenone and 164.6 g. of triethylphosphonoacetate in 1 l. of dimethylformamide are combined with 22 g. of an 80% strength sodium hydride - oil suspension in incremental portions and stirred for 20 hours at room temperature. The solution is then poured on 2 l of 1N hydrochloric acid, extracted with ether, and fractionated after evaporation of the solvent. The product at 126°–146°/0.04 torr is the ethyl ester of 3-(4-methoxyphenyl)-crotonic acid (87 g.). The ester is hydrogenated in 400 ml. of ethyl acetate with 5 g. of palladium/charcoal (10%) under normal pressure, yielding the ethyl ester of 3-(4-methoxyphenyl)-butyric acid (83 g.). Then, a reduction is conducted with 15 g. of lithium aluminum hydride in 600 ml. of ether to obtain 3-(4methoxy-phenyl)-butanol (64 g.). By treatment with thionyl chloride (1 hour at room temperature, then evaporation of the excess thionyl chloride at 14 torr), 64 g. of 3-(4-methoxyphenyl)-1-chlorobutane is obtained. The halogenide is added to an imidazole solution prepared analogously to Example 70 from 33 g. of imidazole and 14.5 g. of a sodium hydride - oil suspension (80%). 4.8 g. of sodium iodide is added to the solution. The latter is heated for 3 hours at 80°, allowed to stand for 2 days at room temperature, and then worked up as set forth in Example 57. The crude product is distilled at 120° (air bath temperature)/0.04 torr on a bulb tube.

| Yield: 57 g. Analysis: | C | H | N |
|---|---|---|---|
| Calculated | 73.01 | 7.88 | 12.17 |
| Found | 71.99 | 8.09 | 11.81 |

3.7 g. of this product is refluxed with 40 ml. of 48% hydrobromic acid for 3.5 hours. After evaporation at 14 torr, the residue is neutralized with potassium bicarbonate solution and extracted with methylene chloride. Evaporation yields 2.65 g. of 4-[3-(1-imidazolyl)-1-methylpropyl]-phenol, m.p. 108°–112°.

Analogously to Example 56, 348 mg. of this starting materials yields, with the use of 210 mg. of 4-methylbenzyl chloride, 416 mg. of the desired product; m.p. 120°–127° (from acetonitrile/toluene).

The following compounds are prepared analogously to Example 75:
(2,4-dichlorobenzyl)-{2-[3-(1-imidazolyl)-1-methylpropyl]-phenyl}-ether
(3,4-dichlorobenzyl)-{2-[3-(1-imidazolyl)-1-methylpropyl]-phenyl}-ether
(2,4-dichlorobenzyl)-{2-[3-(1-imidazolyl)-1-propylpropyl]-phenyl}-ether
(3,4-dichlorobenzyl)-{2-[3-(1-imidazolyl)-1-propylpropyl]-phenyl}-ether.

EXAMPLE 76

(2,4-Dichlorobenzyl)-{4-[3-(1-imidazolyl)-1-propyl]-phenyl}-sulfide

Analogously to Example 75, 12 g. of 1-[3-(4-nitrophenyl)-propyl]-imidazole is obtained from 19.9 g. of 3-(4-nitrophenyl)-1-chloropropane, 10 g. of imidazole, and 4.5 g. of sodium hydride - oil suspension (80%). This product is reduced to 4-[3-(1-imidazolyl)-propyl]-aniline analogously to Example 67 (9.5 g.). Analogously to Example 70, 1.52 g. of this product is reacted to obtain the desired final compound.

| Analysis: | C | H | N |
|---|---|---|---|
| Calculated | 59.20 | 4.92 | 7.67 |
| Found | 59.90 | 4.50 | 7.35 |

The following compounds are obtained in accordance with Example 76:
(3,4-dichlorobenzyl)-{2-[2-(1-imidazolyl)-ethyl]-4-methoxyphenyl}-sulfide
(3,4-dichlorobenzyl)-{2-[3-(1-imidazolyl)-propyl[-4-methoxyphenyl}-sulfide
(3,4-dichlorobenzyl)-{2-[1-ethyl-2-(1-imidazolyl)-ethyl]-4-methoxyphenyl}-sulfide
(3,4-dichlorobenzyl)-{2-[3-(1-imidazolyl)-1-methylpropyl]-4-methoxyphenyl}-sulfide.

EXAMPLE 77

{5-Bromo-4-[3-(1-imidazolyl)-propyl]-2-methoxyphenyl}-(2,4-dichlorobenzyl)-ether, Hydrochloride 16.6 g. of vanillin, 22.4 g. of triethylphosphonoacetate, and 5.75 g. of sodium hydride - oil suspension (80%) in 100 ml. of dimethylformamide are reacted analogously to Example 75. Reaction time: 6 hours at 100°. 21 g. of the thus-obtained ethyl ester of 3-(4-hydroxy-3-methoxyphenyl)-acrylic acid is hydrogenated as described in Example 75. 10 g. of the thus-formed ethyl ester of 3-(4-hydroxy-3-methoxyphenyl)-propionic acid is combined in 100 ml. of dimethylformamide with 1.34 g. of sodium hydride - oil suspension (80%), and after 15 minutes at room temperature, 8.8 g. of 2,4-dichlorobenzyl chloride is added thereto. After 2 hours at room temperature, the mixture is poured on 1N sulfuric acid and extracted with ethyl acetate. After drying and evaporation, 17 g. of the ethyl ester of 3-[4-(2,4-dichlorobenzyloxy)-3-methoxyphenyl]-propionic acid is obtained and slowly combined in 200 ml. ether with 7.1 g. Br in 10 ml. of carbon tetrachloride. After the bromine coloring has disappeared, the mixture is extracted with water and potassium bicarbonate solution, and the ether phase is dried and evaporated. After recrystallization from ethanol, 13.9 g. of the ethyl ester of 3-[2-bromo-4-(2,4-dichlorobenzyloxy)-5-methoxyphenyl]-propionic acid is obtained, m.p. 102°–106° By lithium aluminum hydride reduction of 10 g. of this compound in tetrahydrofuran, 7.5 g. of 3-[2-bromo-4-(2,4-dichlorobenzyloxy)-5-methoxyphenyl]-1-propanol is obtained, m.p. 102°–103°. This product is reacted analogously to Example 75 with thionyl chloride and then with sodium imidazole to obtain the final product. Yield: 2.72 g.; m.p. 142°–144° (from acetonitrile).

EXAMPLE 78

{4-Chloro-2-[3-(1-imidazolyl)-1-phenylpropyl]-phenyl}-(3,4-dichlorobenzyl)-ether Analogously to Example 75, this compound is obtained by using 5-chloro-2-methoxybenzophenone and 3,4-dichlorobenzyl chloride.

EXAMPLE 79

(2,4-Dichlorobenzyl)-{4-[3-(1-imidazolyl)-1-(4-methylphenyl)-propyl]-phenyl}-ether Analogously to Example 75, this substance is prepared by the use of 4-hydroxy-4'-methoxybenzophenone and 2,4-dichlorobenzyl chloride.

EXAMPLE 80

{4-[1-(4-Chlorophenyl)-3-(1-imidazolyl)-propyl]-phenyl}-(3,4-dichlorobenzyl)-ether This compound is produced analogously to Example 75 using 4-chloro-4'-methoxybenzophenone and 3,4-dichlorobenzyl chloride.

EXAMPLE 81

Composition for a Cream

2% (3,4-Dichlorobenzyl)-[2-(1-imidazolylmethyl)-phenyl]-sulfide, hydrochloride
5% Propylene glycol
5% Glycerin stearate
5% Spermaceti
10% Isopropyl palmitate
4% Polysorbate 60
69% Demineralized water

EXAMPLE 82

Composition for a Cream

5% (2,4-Dichlorobenzyl)-{2-[1-(1-imidazolyl)-butyl]-phenyl}-ether
3% "Myrj" 52 (Trademark of Atlas Chemical Industries, Inc. for a series of non-ionic, low-melting point, waxy surface-active agents which are essentially neutral polyoxyethylene derivatives of fat-forming fatty acids)
10% White vaseline
10% Viscous vaseline
8% "Lorol" C 18 (Stearyl alcohol)
0.3% "Carbopol" 934 (Carboxyvinyl polymer)
0.07% NaOH
0.1% "Titriplex" III (Disodium salt of ethylene diamine tetraacetic acid)
0.1% "Nipagin"/"Nipasol" (Mixture of p-Hydroxybenzoic acid methyl ester and p-Hydroxybenzoic acid n-propyl ester) 7 + 3 demineralized water
0.05% "Crematest" perfume oil 6580
63.38% Demineralized water The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. An imidazole of the formula

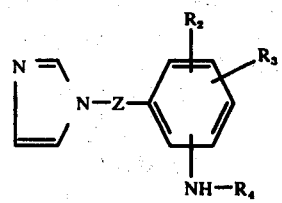

wherein Z is a direct bond or

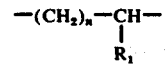

wherein $n$ is the integer 0, 1 or 2 and $R_1$ is hydrogen atom, alkyl of 1–6 carbon atoms, phenyl or phenyl substituted by one to three of halogen atoms, alkyl of 1–6 carbon atoms, alkoxy of 1–6 carbon atoms and nitro; $R_2$ and $R_3$ each are hydrogen atoms, alkyl of 1–10 carbon atoms, alkoxy of 1–6 carbon atoms, alkylmercapto of 1–6 carbon atoms, halogen atoms or nitro, or collectively are $C_4H_4$; $R_4$ is (a) phenyl or phenyl substituted by one to three of halogen atoms, nitro, trifluoromethyl, alkyl of 1–6 carbon atoms and alkoxy of 1–6 carbon atoms, or (b) phenylalkyl of 1–4 carbon atoms in the alkyl group wherein phenyl is unsubstituted or substituted by one to three of halogen atoms, nitro, trifluromethyl, alkyl of 1–6 carbon atoms and alkoxy of 1–6 carbon atoms; and the physiologically acceptable acid addition salts thereof.

2. N-(2,4-Dichlorobenzyl)-2-(1-imidazolylmethyl)-aniline, a compound of claim 1.
3. N-(2,4-Dichlorobenzyl)-4-(1-imidazolylmethyl)-aniline, a compound of claim 1.
4. N-(2,4-Dichlorobenzyl)-2-(1-imidazolyl)-aniline, a compound of claim 1.
5. N-(2,4-Dichlorobenzyl)-4-(1-imidazolyl)-aniline, hydrochloride, dihydrate, a compound of claim 1.
6. An imidazole of the formula

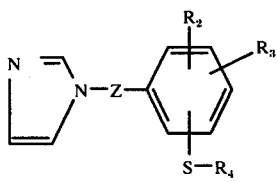

wherein Z is a direct bond or

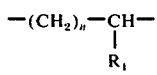

wherein n is the integer 0, 1 or 2 and $R_1$ is a hydrogen atom, alkyl of 1–6 carbon atoms, phenyl or phenyl substituted by one to three of halogen atoms, alkyl of 1–6 carbon atoms, alkoxy of 1–6 carbon atoms and nitro; $R_2$ and $R_3$ each are hydrogen atoms, alkyl of 1–10 carbon atoms, alkoxy of 1–6 carbon atoms, alkylmercapto of 1–6 carbon atoms, halogen atoms or nitro, or collectively are $C_4H_4$; $R_4$ is (a) phenyl or phenyl substituted by one to three of halogen atoms, nitro, trifluoromethyl, alkyl of 1–6 carbon atoms and alkoxy of 1–6 carbon atoms, or (b) phenylalkyl of 1–4 carbon atoms in the alkyl group wherein phenyl is unsubstituted or substituted by one to three of halogen atoms, nitro, trifluoromethyl, alkyl of 1–6 carbon atoms and alkoxy of 1–6 carbon atoms, and the physiologically acceptable acid addition salts thereof.

7. (2,4-Dichlorobenzyl)-[2-(1-imidazolylmethyl)-phenyl[-sulfide, hydrochloride, a compound of claim 6.
8. (3,4-Dichlorobenzyl)-{2-[1-(1-imidazolyl)-butyl[-phenyl}-sulfide, a compound of claim 6.
9. (3-Chlorobenzyl)-{2-[1-(1-imidazolyl)-butyl]-phenyl}-sulfide, a compound of claim 6.
10. (3,4-Dichlorobenzyl)-{2-[1-(1-imidazolyl)-butyl]-4-methoxyphenyl}-sulfide, a compound of claim 6.
11. (3-Chlorobenzyl)-{2-[1-(1-imidazolyl)-butyl-4-methoxyphenyl}-sulfide, a compound of claim 6.
12. 4-Chloro-2'-(1-imidazolylmethyl)-diphenyl sulfide, hydrochloride, a compound of claim 6.
13. Benzyl-[2-(1-imidazolymethyl)-phenyl]-sulfide, hydrochloride, a compound of claim 6.
14. (4-Chlorobenzyl)-[2-(1-imidazolymethyl)-phenyl]-sulfide, hydrochloride, a compound of claim 6.
15. (3-Chlorobenzyl)-[2-(1-imidazolylmethyl)-phenyl]-sulfide, hydrochloride, a compound of claim 6.
16. (3,4-Dichlorobenzyl)-[2-(1-imidazolylmethyl)-phenyl]-sulfide, hydrochloride, a compound of claim 6.
17. (2,4-Dichlorobenzyl)-[4-(1-imidazolyl)-phenyl]-sulfide, a compound of claim 6.
18. (2,4-Dichlorobenzyl)-[2-(1-imidazolyl)-phenyl]-sulfide, a compound of claim 6.
19. (3-Chlorobenzyl)-[2-(1-imidazolyl)-phenyl]-sulfide, a compound of claim 6.

20. (3,4-Dichlorobenzyl)-[2-(1-imidazolyl)-phenyl]-sulfide, a compound of claim 6.
21. (3,4-Dichlorophenyl)-[2-(1-imidazolyl)-phenyl]-sulfide, a compound of claim 6.
22. (3,4-Dichloro-γ-methylbenzyl)-[2-(1-imidazolyl)-phenyl]-sulfide, a compound of claim 6.
23. (2,4-Dichlorobenzyl)-{4-[3-(1-imidazolyl)-1-propyl]-phenyl}-sulfide, a compound of claim 6.
24. (3,4-Dichlorobenzyl)-{2-[2-(1-imidazolyl)-ethyl]-4-methoxyphenyl}-sulfide, a compound of claim 6.
25. (3,4-Dichlorobenzyl)-{2-[3-(1-imidazolyl)-propyl]-4-methoxyphenyl}-sulfide, a compound of claim 6.
26. (3,4-Dichlorobenzyl)-{2-[1-ethyl-2-(1-imidazolyl)-ethyl]-4-methoxyphenyl}-sulfide, a compound of claim 6.
27. (3,4-Dichlorobenzyl)-{2-[3-(1-imidazolyl)-1-methylpropyl]-4-methoxyphenyl}-sulfide, a compound of claim 6.
28. An imidazole of the formula

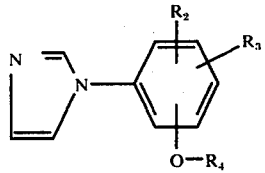

wherein $R_2$ and $R_3$ each are hydrogen atoms, alkyl of 1–10 carbon atoms, alkoxy of 1–6 carbon atoms, alkylmercapto of 1–6 carbon atoms, halogen atoms or nitro, or collectively are $C_4H_4$; $R_4$ is (a) alkenyl of 3–6 carbon atoms, (b) alkinyl of 3–6 carbon atoms, (c) phenyl or phenyl substituted by one to three of halogen atoms, nitro, trifluoromethyl, alkyl of 1–6 carbon atoms and alkoxy of 1–6 carbon atoms, or (d) phenylalkyl of 1–4 carbon atoms in the alkyl group wherein phenyl is unsubstituted or substituted by one to three of halogen atoms, nitro, trifluoromethyl, alkyl of 1–6 carbon atoms, or alkoxy of 1–6 carbon atoms; or (e) alkyl of 1–6 carbon atoms; and the physiologically acceptable acid addition salts thereof.

29. Allyl-[2-(1-imidazolyl)-phenyl]-ether, hydrochloride, a compound of claim 28.
30. [2-(1-Imidazolyl)-phenyl]-(2-propinyl)-ether, a compound of claim 28.
31. [2-(1-Imidazolyl)-phenyl]-(4-methylbenzyl)-ether, a compound of claim 28.
32. [2-(1-Imidazolyl)-phenyl]-(4-methoxybenzyl)-ether, a compound of claim 28.
33. (2,4-Dichlorobenzyl)-[2-(1-imidazolyl)-phenyl]-ether, hydrochloride, a compound of claim 28.
34. (2,4-Dichlorobenzyl)-[4-(1-imidazolyl)-phenyl]-ether, hydrochloride, a compound of claim 28.
35. [2-(1-Imidazolyl)-phenyl]-2-nitrobenzyl ether, a compound of claim 28.
36. [2-(1-Imidazolyl)-phenyl]-[3-(trifluoromethyl)-benzyl]-ether, hydrochloride, a compound of claim 28.
37. (3,4-Dichlorobenzyl)-[2-(1-imidazolyl)-4-methylphenyl]-ether, sulfate, a compound of claim 28.
38. (2,4-Dichlorobenzyl)-[2-(1-imidazolyl)-4-nitrophenyl]-ether, a compound of claim 28.
39. [4-Chloro-2-(1-imidazolyl)-phenyl]-2,4-dichlorobenzyl)-ether, a compound of claim 28.

40. [4-Chloro-2-(1-imidazolyl)-phenyl]-(3,4-dichlorobenzyl)-ether, a compound of claim 28.

41. [5-Chloro-2-(1-imidazolyl)-phenyl]-(3,4-dichlorobenzyl)-ether, a compound of claim 28.

42. [4-Chloro-2-(1-imidazolyl)-phenyl]-(3,4-dichloro-α-methylbenzyl)-ether, a compound of claim 28.

43. (3,4-Dichlorobenzyl)-[3,5-dichloro-2-(1-imidazolyl)-phenyl]-ether, a compound of claim 28.

44. 4-(1-Imidazolyl)-diphenyl ether, hydrochloride, a compound of claim 28.

45. An imidazole of the formula

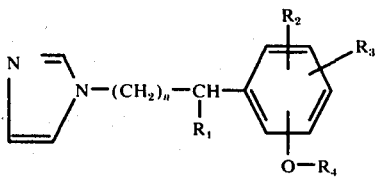

wherein $n$ is the integer 0, 1 or 2 and $R_1$ is a hydrogen atom, alkyl of 1–6 carbon atoms, phenyl or phenyl substituted by one to three of halogen atoms, alkyl of 1–6 carbon atoms and alkoxy of 1–6 carbon atoms; $R_2$ and $R_3$ each are hydrogen atoms, alkyl of 1–10 carbon atoms, alkoxy of 1–6 carbon atoms, alkylmercapto of 1–6 carbon atoms, halogen atoms or nitro, or collectively are $C_4H_4$; $R_4$ is phenylalkyl of 1–4 carbon atoms in the alkyl group wherein phenyl is unsubstituted or substituted by one to three of halogen atoms, nitro, trifluoromethyl, alkyl of 1–6 carbon atoms and alkoxy of 1–6 carbon atoms; and the physiologically acceptable acid addition salts thereof.

46. A compound of claim 45 wherein $R_1$ is alkyl of 1–6 carbon atoms.

47. A compound of claim 45 wherein $n$ is 0.

48. [4-(1-Imidazolylmethyl)-phenyl]-benzyl ether, a compound of claim 45.

49. [4-(1-Imidazolylmethyl)-phenyl]-(2-nitrobenzyl)-ether, hydrochloride, a compound of claim 45.

50. [4-(1-Imidazolylmethyl)-phenyl]-(p-tolylmethyl)-ether, a compound of claim 45.

51. [4-(1-Imidazolylmethyl)-phenyl]-(4-methoxybenzyl)-ether, a compound of claim 45.

52. (4-Chlorobenzyl)-[4-(1-imidazolylmethyl)-phenyl]-ether, a compound of claim 45.

53. (2,4-Dichlorobenzyl)-[4-(1-imidazolylmethyl)-phenyl]-ether, a compound of claim 45.

54. (2,6-Dichlorobenzyl)-[4-(1-imidazolylmethyl)-phenyl]-ether, hydrochloride, a compound of claim 45.

55. (4-Bromobenzyl)-[4-(1-imidazolylmethyl)-phenyl]-ether, a compound of claim 45.

56. [4-(1-Imidazolylmethyl)-phenyl]-(3-trifluoromethylbenzyl)-ether, hyperchlorate, a compound of claim 45.

57. (2,4-Dichlorobenzyl)-[2-(1-imidazolylmethyl)-phenyl]-ether, a compound of claim 45.

58. (2,4-Dichlorobenzyl)-[3-(1-imidazolylmethyl)-phenyl]-ether, a compound of claim 45.

59. [4-Bromo-2-(1-imidazolylmethyl)-phenyl]-(2,4-dichlorobenzyl)-ether, hydrochloride, a compound of claim 45.

60. [4-Chloro-2-(1-imidazolylmethyl)-phenyl]-(3,4-dichlorobenzyl)-ether, a compound of claim 45.

61. (3,4-Dichlorobenzyl)-[3,5-dichloro-2-(1-imidazolylmethyl)-phenyl]-ether, a compound of claim 45.

62. [4-Chloro-2-(1-imidazolylmethyl)-phenyl]-(2,4-dichlorobenzyl)-ether, a compound of claim 45.

63. [4,6-Dibromo-2-(1-imidazolylmethyl)-phenyl]-(2,4-dichlorobenzyl)-ether, hydrochloride, a compound of claim 45.

64. (2,4-Dichlorobenzyl)-[2-(1-imidazolylmethyl)-4-methylphenyl]-ether, a compound of claim 45.

65. (2,4-Dichlorobenzyl)-]2-(1-imidazolylmethyl)-4-(1,1,3,3-tetramethylbutyl)-phenyl]-ether, hydrochloride, a compound of claim 45.

66. (2,4-Dichlorobenzyl)-[4-(1-imidazolylmethyl)-2-methoxyphenyl]-ether, a compound of claim 45.

67. (2,4-Dichlorobenzyl)-[2-(1-imidazolylmethyl)-4-methylthiophenyl]-ether, a compound of claim 45.

68. (2,4-Dichlorobenzyl)-[3-(1-imidazolylmethyl)-2-naphthyl]-ether, a compound of claim 45.

69. [4-(1-Imidazolylmethyl)-2-nitrophenyl]-(2,4-dichlorobenzyl)-ether, a compound of claim 45.

70. (2,4-Dichlorobenzyl)-{4-[α-(1-imidazolyl)-benzyl]-phenyl}-ether, hydroperchlorate, a compound of claim 45.

71. (3-Chlorobenzyl)-{2-[1-(1-imidazolyl)-propyl]-phenyl}-ether, a compound of claim 45.

72. (3,4-Dichlorobenzyl)-{2-[1-(1-imidazolyl)-propyl]-phenyl}-ether, a compound of claim 45.

73. (3-Chlorobenzyl)-{2-[1-(1-imidazolyl)-2-methyl)-propyl]-phenyl}-ether, a compound of claim 45.

74. (3,4-Dichlorobenzyl)-{2-[1-(1-imidazolyl)-2-methylpropyl]-phenyl}-ether, a compound of claim 45.

75. (3,4-Dichlorobenzyl)-{2-[1-(1-imidazolyl)-pentyl]-phenyl}-ether, a compound of claim 45.

76. (2,4-Dichlorobenzyl)-{4-[α-(1-imidazolyl)-4-methylbenzyl]-phenyl}-ether, a compound of claim 45.

77. (2,4-Dichlorobenzyl)-{2-[2,4-dimethoxy-α-(1-imidazolyl)-benzyl]-5-methoxyphenyl}-ether, a compound of claim 45.

78. {2-[4-Chloro-α-(1imidazolyl)-benzyl]-5-methoxyphenyl}-(2,4-dichlorobenzyl)-ether, a compound of claim 45.

79. (2,4-Dichlorobenzyl)-{4-[α-(1-imidazolyl)-4-nitrobenzyl]-phenyl}-ether, a compound of claim 45.

80. (2,4-Dichlorobenzyl)-{4-[1-(1-imidazolyl)-ethyl]-phenyl}-ether, hydroperchlorate, a compound of claim 45.

81. (3-Chlorobenzyl)-{2-[1-(1-imidazolyl)-ethyl]-phenyl}-ether, a compound of claim 45.

82. (3,4-Dichlorobenzyl)-{2-[1-(1-imidazolyl)-ethyl]-phenyl}-ether, a compound of claim 45.

83. (2,4-Dichlorobenzyl)-{2-[1-(1-imidazolyl)-butyl]-phenyl}-ether, a compound of claim 45.

84. (3-Chloro-α-methylbenzyl)-{2-[1-(1-imidazolyl)-butyl]-phenyl}-ether, a compound of claim 45.

85. (3,4-Dichloro-α-methylbenzyl)-{2-[1-(1-imidazolyl)-butyl]-phenyl}-ether, a compound of claim 45.

86. (3-Chlorobenzyl)-{5-chloro-2-[1-(1-imidazolyl)-butyl]-phenyl}-ether, a compound of claim 45.

87. {5-Chloro-2-[1-(1-imidazolyl)-butyl]-phenyl}-(3,4-dichlorobenzyl)-ether, a compound of claim 45.

88. (3-Chlorobenzyl)-{4-chloro-2-[1-(1-imidazolyl)-butyl]-phenyl}-ether, a compound of claim 45.

89. {4-Chloro-2-[1-(1-imidazolyl)-butyl]-phenyl}-(3,4-dichlorobenzyl)-ether, a compound of claim 45.

90. {4-Chloro-2-[1-(1-imidazolyl)-butyl]-phenyl}-(2,4-dichlorobenzyl)-ether, a compound of claim 45.
91. (3-Chlorobenzyl)-{3,5-dichloro-2-[1-(1-imidazolyl)-butyl]-phenyl}-ether, a compound of claim 45.
92. (2,4-Dichlorobenzyl)-{3,5-dichloro-2-[1-(1-imidazolyl)-butyl]-phenyl}-ether, a compound of claim 45.
93. (3,4-Dichlorobenzyl)-{3,5-dichloro-2-[1-(1-imidazolyl)-butyl]-phenyl}-ether, a compound of claim 45.
94. (3-Chlorobenzyl)-{4,5-dichloro-2-[1-(1-imidazolyl)-butyl]-phenyl}-ether, a compound of claim 45.
95. (2,4-Dichlorobenzyl)-{4,5-dichloro-2-[1-(1-imidazolyl)-butyl]-phenyl}-ether, a compound of claim 45.
96. (3,4-Dichlorobenzyl)-{4,5-dichloro-2-[1-(1-imidazolyl)-butyl]-phenyl}-ether, a compound of claim 45.
97. {4-Chloro-2-[α-(1-imidazolyl)-benzyl]-phenyl}-(2,4-dichlorobenzyl)-ether, a compound of claim 45.
98. (4-Bromobenzyl)-[4-bromo-2-(1-imidazolylmethyl)-phenyl]-ether, hydrochloride, a compound of claim 45.
99. (2,4-Dichlorobenzyl)-[4-chloro-2-(1-imidazolylmethyl)-phenyl]-ether, a compound of claim 45.
100. [5-Bromo-2-(1-imidazolylmethyl)-phenyl]-(2,4-dichlorobenzyl)-ether, a compound of claim 45.
101. (2,4-Dichlorobenzyl)-{2-[1-(1-imidazolyl)-butyl]-phenyl}-ether, nitrate, a compound of claim 45.
102. (3-Chlorobenzyl)-{2-[1-(1-imidazolyl)-butyl]-phenyl}-ether, hydrochloride, a compound of claim 45.
103. (3,4-Dichlorobenzyl)-{2-[1-(1-imidazolyl)-butyl]-phenyl}-ether, hydrochloride, a compound of claim 45.
104. (4-Bromobenzyl)-{2-[1-(1-imidazolyl)-butyl]-phenyl}-ether, hydrochloride, a compound of claim 45.
105. (2,4-Dichlorobenzyl)-{2-[1-(1-imidazolyl)-heptyl]-phenyl}-ether, hydrochloride, a compound of claim 45.
106. (2,4-Dichlorobenzyl)-{2-[1-(1-imidazolyl)-ethyl]-phenyl}-ether, a compound of claim 45.
107. Benzyl-{4-[1-(1-imidazolyl)-butyl]-phenyl}-ether, a compound of claim 45.
108. (3,4-Dichlorobenzyl)-[4-(1-imidazolylmethyl)-phenyl]-ether, hydrochloride, a compound of claim 45.
109. (2,4-Dichlorobenzyl)-[2,6-dichloro-4-(1-imidazolylmethyl)-phenyl]-ether, a compound of claim 45.
110. (3,4-Dichloro-α-methylbenzyl)-[2-(1-imidazolylmethyl)-phenyl]-ether, hydrochloride, a compound of claim 45.
111. (2,4-Dichlorobenzyl)-{4-[2-(1-imidazolyl)-ethyl]-phenyl}-ether, hydrochloride, a compound of claim 45.
112. (2,4-Dichlorobenzyl)-{2-[2-(1-imidazolyl)-ethyl]-phenyl}-ether, hydrochloride, a compound of claim 45.
113. (2,4-Dichlorobenzyl)-{2-[1-ethyl-2-(1-imidazolyl)-ethyl]-phenyl}-ether, a compound of claim 45.
114. (3,4-Dichlorobenzyl)-{2-[1-ethyl-2-(1-imidazolyl)-ethyl]-phenyl}-ether, a compound of claim 45.
115. (2,4-Dichlorobenzyl)-{2-[2-(1-imidazolyl)-1-propylethyl]-phenyl}-ether, a compound of claim 45.
116. (3,4-Dichlorobenzyl)-{2-[2-(1-imidazolyl)-1-propylethyl]-phenyl}-ether, a compound of claim 45.
117. (2,4-Dichlorobenzyl)-{2-[3-(1-imidazolyl)-propyl]-phenyl}-ether, hydrochloride, hydrate, a compound of claim 45.
118. (2,4-Dichlorobenzyl)-{2-[3-(1-imidazolyl)-1-methylpropyl]-phenyl}-ether, a compound of claim 45.
119. (3,4-Dichlorobenzyl)-{2-[3-(1-imidazolyl)-1-methylpropyl]-phenyl}-ether, a compound of claim 45.
120. (2,4-Dichlorobenzyl)-{2-[3-(1-imidazolyl)-1-propylpropyl]-phenyl}-ether, a compound of claim 45.
121. (3,4-Dichlorobenzyl)-{2-[3-(1-imidazolyl)-1-propylpropyl]-phenyl}-ether, a compound of claim 45.
122. {5-Bromo-4-[3-(1-imidazolyl)-propyl]-2-methoxyphenyl}-(2,4-dichlorobenzyl)-ether, hydrochloride, a compound of claim 45.
123. {4-Chloro-2-[3-(1-imidazolyl)-1-phenylpropyl]-phenyl}-(3,4-dichlorobenzyl)-ether, a compound of claim 45.
124. (2,4-Dichlorobenzyl)-{4-[3-(1-imidazolyl)-1-(4-methylphenyl)-propyl]-phenyl}-ether, a compound of claim 45.
125. {4-[1-(4-Chlorophenyl)-3-(1-imidazolyl)-propyl]-phenyl}-(3,4-dichlorobenzyl)-ether, a compound of claim 45.
126. {4-[3-(1-Imidazolyl)-1-methylpropyl]-phenyl}-(4-methylbenzyl)-ether, hydrochloride, a compound of claim 45.
127. An imidazole of the formula

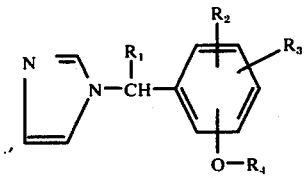

wherein $R_1$ is a hydrogen atom or alkyl of 1–6 carbon atoms; $R_2$ and $R_3$ each are hydrogen atoms, alkyl of 1–10 carbon atoms, alkoxy of 1–6 carbon atoms, alkylmercapto of 1–6 carbon atoms, halogen atoms or nitro, or collectively are $C_4H_4$; and $R_4$ is phenyl or phenyl substituted by one to three of halogen atoms, nitro, trifluoromethyl, alkyl of 1–6 carbon atoms and alkoxy of 1–6 carbon atoms; and the physiologically acceptable acid addition salts thereof.

128. 2-(1-Imidazolylmethyl)-diphenyl ether, hydrochloride, a compound of claim 127.
129. 4-Chloro-2'-(1-imidazolylmethyl)-diphenyl ether, hydrochloride, a compound of claim 127.
130. An imidazole of the formula

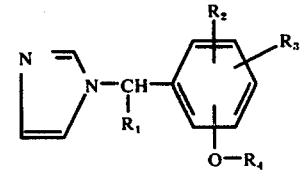

wherein $R_1$ is a hydrogen atom or alkyl of 1–6 carbon atoms; $R_2$ and $R_3$ each are hydrogen atoms, alkyl of 1–10 carbon atoms, alkoxy of 1–6 carbon atoms, alkylmercapto of 1–6 carbon atoms, halogen atoms or nitro, or collectively are $C_4H_4$; and $R_4$ is alkenyl of 3–6 carbon atoms or alkinyl of 3–6 carbon atoms; and the physiologically acceptable acid addition salts thereof.

131. [4-(1-Imidazolylmethyl)-phenyl]-(2-propinyl)-ether, a compound of claim 130.

132. [4-(1-Imidazolylmethyl)-phenyl]-(2-propenyl)-ether, hydroperchlorate, a compound of claim 130.

133. Hexyl-[4-(1-imidazolylmethyl)-phenyl]-ether, hydroperchlorate.

134. A pharmaceutical composition adapted for the treatment of fungal, bacterial and yeast infections in animals comprising, in admixture with a pharmaceutical carrier, an amount effective to treat such an infection of an imidazole of the formula

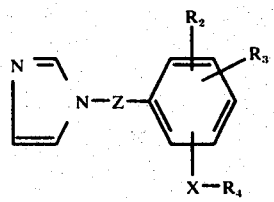

wherein $R_2$ and $R_3$ each are hydrogen atoms, alkyl of 1–10 carbon atoms, alkoxy of 1-6 1-6 atoms, alkylmercapto of 1–6 carbon atoms, halogen atoms or nitro, or collectively are $C_4H_4$; and I. X is NH, Z is a direct bond or

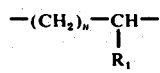

wherein $n$ is the integer 0, 1 or 2 and $R_1$ is a hydrogen atom, alkyl of 1–6 atoms, phenyl or phenyl substituted by one to three of halogen atoms, alkyl of 1–6 carbon atoms, alkoxy of 1–6 carbon atoms and nitro groups; and $R_4$ is (a) phenyl or phenyl substituted by one to three of halogen atoms, nitro, trifluormethyl, alkyl of 1–6 carbon atoms and alkoxy of 1–6 carbon atoms, or (b) phenylalkly of 1–4 carbon atoms in the alkyl group wherein phenyl is unsubstituted or substituted by one to three of halogen atoms, nitro, trifluoromethyl, alkyl of 1–6 carbon atoms and alkoxy of 1–6 carbon atoms; or II. X is S and Z, $R_1$ and $R_4$ are as defined in I, above, or III. X is O, Z is a direct bond and $R_4$ is (a) alkenyl of 3–6 carbon atoms, (b) alkinyl of 3–6 carbon atoms, (c) phenyl or phenyl substituted by one to three of halogen atoms, nitro, trifluoromethyl, alkyl of 1–6 carbon atoms and alkoxy of 1–6 carbon atoms, or (d) phenylalkyl of 1–4 carbon atoms in the alkyl group wherein phenyl is unsubstituted or substituted by one to three of halogen atoms, nitro, trifluoromethyl, alkyl of 1–6 carbon atoms and alkoxy of 1–6 carbon atoms; or (e) alkyl of 1–6 carbon atoms; or IV. X is O, Z is

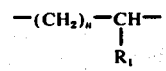

wherein $n$ is the integer 0, 1 or 2 and $R_1$ is phenyl or phenyl substituted by one to three of halogen atoms, alkyl of 1–6 carbon atoms and alkoxy of 1–6 carbon atoms, and $R_4$ is phenylalkyl of 1–4 carbon atoms in the alkyl group wherein phenyl is unsubstituted or substituted by one to three of halogen atoms, nitro, trifluoromethyl, alkyl of 1–6 carbon atoms and alkoxy of 1–6 carbon atoms; or V. X is O, Z is

wherein $R_1$ is H or alkyl of 1–6 carbon atoms, and $R_4$ is phenyl or phenyl substituted by one to three of halogen atoms, nitro, trifluoromethyl, alkyl of 1–6 carbon atoms and alkoxy of 1–6 carbon atoms; or VI. X is O, Z is

wherein $R_1$ is a hydrogen atom or alkyl of 1–6 carbon atoms, and $R_4$ is alkenyl of 3–6 carbon atoms or alkinyl of 3–6 carbon atoms; or a physiologically acceptable salt thereof.

135. A method of treating fungal, bacterial and yeast infections in animals which comprises administering to the infected animal an amount of a composition of claim 134 effective to combat the infection.

136. A method according to claim 134 wherein the infection is a dermatophyte infection.

* * * * *